United States Patent

Nishimoto et al.

[11] Patent Number: 6,030,883
[45] Date of Patent: Feb. 29, 2000

[54] METHOD OF BONDING SUBSTRATES, DETECTOR CELL PRODUCED ACCORDING TO THIS METHOD AND OPTICAL MEASURING APPARATUS HAVING THIS DETECTOR CELL

[75] Inventors: Takahiro Nishimoto, Kyoto; Hiroaki Nakanishi, Nara, both of Japan

[73] Assignee: Shimadzu Corporation, Kyoto, Japan

[21] Appl. No.: 08/859,037

[22] Filed: May 20, 1997

[30] Foreign Application Priority Data

May 22, 1996 [JP] Japan ................................. 8-126991
Mar. 17, 1997 [JP] Japan ................................. 9-063160

[51] Int. Cl.[7] .................................................. H01L 21/265
[52] U.S. Cl. .......................... 438/455; 438/406; 438/456; 438/459
[58] Field of Search .................................. 438/455, 456, 438/459, 406, 977; 148/DIG. 12, DIG. 135, DIG. 150

[56] References Cited

U.S. PATENT DOCUMENTS 5,207,864  5/1993  Bhat et al. ............................... 438/455
5,362,667  11/1994  Linn et al. ............................... 438/455
5,441,591  8/1995  Imuthrn et al. .......................... 438/455

OTHER PUBLICATIONS

Nakanishi, H. et al., Studies on SiO2–SiO2 Bonding with Hydrofluoric Acid–Room Temperature and Low Stress Bonding Technique for MEMS, Proceedings of the Eleventh Annual International Workshop on IEEE Micro Electro Mechanical Systems, pp. 609–614, 1998.

*Primary Examiner*—Carl Whitehead, Jr.
*Assistant Examiner*—Maria Guerrero
*Attorney, Agent, or Firm*—Armstrong, Westerman, Hattori, McLeland & Naughton

[57] ABSTRACT

At a room temperature, cleaned glass substrates 8a, 8b are suitably positioned and placed one upon another. A hydrofluoric acid solution or alkaline solution 10 is dropped into the bonding interface between the glass substrates 8a, 8b. The hydrofluoric acid solution or alkaline solution thus dropped spreads along the bonding interface. At a room temperature, a load is then applied to the upper glass substrate 8a and allowed to stand for a suitable period of time, thus bonding the glass substrates to each other.

10 Claims, 5 Drawing Sheets

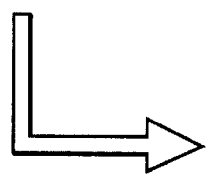

METHOD OF BONDING SUBSTRATES, DETECTOR CELL PRODUCED ACCORDING TO THIS METHOD AND OPTICAL MEASURING APPARATUS HAVING THIS DETECTOR CELL

BACKGROUND OF THE INVENTION

1. Field of the Invention

The present invention relates to a method of mutually bonding substrates of which bonding surfaces contain silicon dioxide as the primary component, a detector cell produced according to this bonding method and an optical measuring apparatus, such as a capillary electrophoresis apparatus or the like, having this detector cell.

2. Description of the Related Art

To bond glass substrates to each other, there has conventionally been widely used a fusion-bonding method by which the glass substrates are heated to a temperature of the glass annealing point or more such that the glass substrates are bonded as fused. For example, substrates of borosilicate glass (Pyrex 7740 or the like) are fusion-bonded when heated to a temperature of about 560° C. or more, and substrates of quartz are fusion-bonded when heated to a temperature of about 1200° C. or more.

There is also disclosed an optical measuring apparatus, such as a capillary electrophoresis apparatus or the like, arranged such that a sample flowing in the passage is analyzed for components by irradiating light such as ultraviolet rays or the like onto the sample and measuring the amount of light absorbed by the sample or the amount of fluorescence emitted from the sample (for example, D. Harrison et al. Analytica Chimica Acta 283 (1993) 361–366). In such an apparatus, a groove is formed in each of a pair of glass substrates and the glass substrates are bonded to each other by the fusion-bonding method above-mentioned, thus forming a passage in which a sample is to flow.

To fusion-bond substrates of quartz, it is required to raise the temperature thereof to a level as high as 1200° C., as mentioned earlier. Disadvantageously, this not only requires a special temperature raising device, but also makes it difficult to hold the quartz substrates of which temperature is being raised to such a level.

To reflect light in a multiple manner to increase the light passage length in an optical measuring apparatus in which grooves formed in the glass substrates serve as the sample passage, metallic layers are formed on the grooves in the glass substrates. Since the glass substrates are bonded to each other at an ultra-high temperature, the metallic layers are changed in quality, thus assuring no sufficient reflection efficiency. In particular, when light in the ultraviolet zone is to be used, the glass substrates to be used are limited to quartz substrates in view of the characteristics of transmittance. Further, it is preferred to use, as each metallic layer, an aluminium layer in view of reflection efficiency. However, quartz is high in melting point while aluminium has a very low degree of heat tolerance. In fusion-bonding, aluminium is therefore changed in quality. Accordingly, it is substantially difficult to use an aluminium layer as the metallic layer.

In fusion-bonding, the substrates are bonded to each other in a point-contact manner. Thus, the application of a load to the substrates is uneven. This makes it difficult to evenly bond the glass substrates in their entirety. Further, the fusion-bonding processing is executed on the glass substrates as conveyed in a thermal processing furnace. This makes it difficult to bond, to each other, the glass substrates as accurately positioned with respect to each other.

In view of the foregoing, the desired passage cannot be formed. Accordingly, the optical measuring apparatus of prior art cannot assure not only a uniform migration of a sample, but also a multiple-reflection of light with a high reflectance. Thus, a satisfactory detection precision cannot be obtained.

SUMMARY OF THE INVENTION

It is an object of the present invention to provide (i) a substrate bonding method capable of readily mutually bonding, at a room temperature, substrates made of a material of glass, quartz or the like of which at least bonding surfaces contain silicon dioxide as the primary component, (ii) a detector cell produced according to this substrate bonding method and (iii) an optical measuring apparatus having this detector cell and capable of achieving a highly precise analysis.

To achieve the object above-mentioned, the present invention provides a method of bonding substrates of which at least bonding surfaces contain silicon dioxide as the primary component, and this substrate bonding method comprises the step of interposing a solution for dissolving the substrates between the bonding surfaces of the substrates. The solution for dissolving the substrates is a hydrofluoric acid solution or an alkaline solution.

Preferably, the hydrofluoric acid solution is a mixed solution of hydrofluoric acid and water, a buffered hydrofluoric acid or an undiluted solution of hydrofluoric acid. Preferably, the alkaline solution is an inorganic alkaline solution of KOH, NaOH, $NH_4OH$ or the like, or an organic alkaline solution such as tetramethylammonium hydroxide or the like.

Preferably, a pair of the substrates to be bonded to each other consists of a pair of quartz and quartz, a pair of quartz and borosilicate glass, a pair of borosilicate glass and borosilicate glass, a pair of quartz and a substrate having an oxide layer of silicon, a pair of substrates each having an oxide layer of silicon and a pair of borosilicate glass and a substrate having an oxide layer of silicon.

There are used a pair of cleaned glass substrates, a groove is formed in at least one of the glass substrates and the glass substrates are bonded to each other according to the substrate bonding method above-mentioned, thus forming a sample passage. Preferably, a metallic layer is formed on the surface of the groove and a protective resist layer is formed on the metallic layer. The metallic layer formed on the surface of the groove causes incident light to be reflected in a multiple manner in the passage before the light is guided to a light emission port. The protective resist layer prevents the metallic layer from being damaged by a hydrofluoric acid solution to be dropped at the next step.

Preferably, the cleaning is cleaning with the use of organic matter of acetone or methanol, cleaning with the use of a mixed solution of $H_2SO_4$ and $H_2O_2$, cleaning with the use of a mixed solution of $NH_4OH$, $H_2O_2$ and water, or cleaning with the use of pure water. In particular, cleanings out of the cleanings above-mentioned may suitably be combined with one another to enhance the cleaning effect.

For example, the substrate bonding method of the present invention is embodied as shown in FIG. 1 corresponding to an embodiment. At a room temperature, a pair of glass substrates 1a, 1b cleaned by the method mentioned above, are placed one upon another as properly positioned. A hydrofluoric acid solution 10 is dropped to the bonding interface between the glass substrates 1a, 1b. The solution 10 thus dropped spreads uniformly along the bonding interface. At a room temperature, a load is then applied to the upper glass substrate, and the glass substrates are allowed to stand for a suitable period of time, thus causing the glass substrates to be bonded to each other.

As shown in FIG. 2 corresponding to another embodiment, a hydrofluoric acid solution 10 is dropped on a lower glass substrate 1b which has been cleaned, and an upper glass substrate 1a is then placed on and suitably positioned with respect to the lower glass substrate 1b. At a room temperature, a load is then applied to the upper glass substrate 1a, and the glass substrates 1a, 1b are allowed to stand for a suitable period of time, thus causing the glass substrates 1a, 1b to be bonded to each other.

The present invention also provides a detector cell which has a sample inlet port, a passage for an introduced sample and a sample outlet port and which uses at least a portion of the passage as a measuring chamber. This detector cell is characterized in that a groove is formed in the bonding surface of at least one glass substrate out of a pair of cleaned glass substrates and that the glass substrates are bonded to each other with a hydrofluoric acid solution or an alkaline solution interposed between the bonding surfaces of the glass substrates. Preferably, a metallic layer is formed on the surface of the groove, and a protective resist layer is formed on the metallic layer.

Preferably, the detector cell is of the type having a sample inlet port, a passage for an introduced sample and a sample outlet port and using at least a portion of the passage as a measuring chamber, and is arranged such that: a groove serving as the passage is formed in the bonding surface of at least one glass substrate out of two glass substrates bonded to each other by the substrate bonding method abovementioned; a first optical reflection layer is formed in an inner surface of the groove at its portion serving as the measuring chamber or on the glass surface under the groove at its portion serving as the measuring chamber; a second optical reflection layer is formed on the bonding surface of the other glass substrate at its position opposite to the first optical reflection layer; and light incidence and emission windows are formed in that portion of the groove which serves as the measuring chamber, whereby light incident upon the passage through the light incidence window is reflected in a multiple manner by the first and second optical reflection layers before the light is left from the light emission window.

The present invention also provides an optical measuring apparatus which has a detector cell having a sample inlet port, a passage for an introduced sample and a sample outlet port and using at least a portion of the passage as a measuring chamber, and which is arranged to measure light transmitted through a sample flowing in the passage to analyze the components of the sample, and this optical measuring apparatus is characterized in that a groove serving as the passage is formed in the bonding surface of at least one glass substrate out of two glass substrates bonded to each other according to the substrate bonding method abovementioned.

According to the present invention, the optical measuring apparatus comprises a light source for irradiating light to the light incidence window of the detector cell, a photodetector for measuring light emitted from the light emission window of the detector cell, and means for positioning the detector cell.

Preferably, the positioning means comprises a concave formed in a stage for holding the detector cell, and the detector cell is removably fitted in the concave.

According to the substrate bonding method of the present invention, glass substrates of various types and silicon substrates each having an oxide layer can be bonded at a room temperature and such bonding can be made through a simpler procedure with no use of special heating device and holding means required in fusion-bonding. In particular, even though grooves are disposed at the glass substrates, and light reflection metallic layers of aluminium or the like are formed on the respective grooves, the glass substrates can be bonded without the metallic layer being damaged.

Further, these substrates are bonded through a hydrofluoric acid solution or alkaline solution which is spread by capillary action at the bonding interface between the substrates. This enables the substrates to be uniformly bonded in their entirety.

Further, when an optical measuring apparatus is formed using the substrate bonding method of the present invention, the light reflection member is not damaged at the time of glass substrate bonding. Thus, the optical measuring apparatus achieves a highly precise analysis.

BRIEF DESCRIPTION OF THE DRAWINGS

FIG. 3 (B) is a section view taken along the line X—X in FIG. 3 (A);

FIG. 3 (C) is a section view taken along the line Y—Y in FIG. 3 (B);

DETAILED DESCRIPTION OF PREFERRED EMBODIMENTS

Figure 1A:
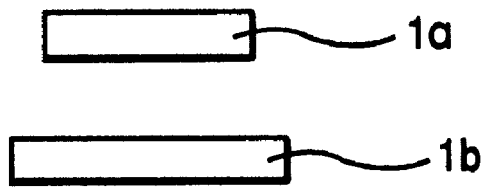
FIG. 1 (A) to FIG. 1 (D) illustrate, with the passage of time, glass substrate bonding steps of a substrate bonding method according to a first embodiment of the present invention.
Figure 1B:
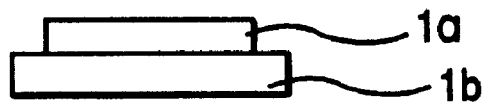
Figure 1C:
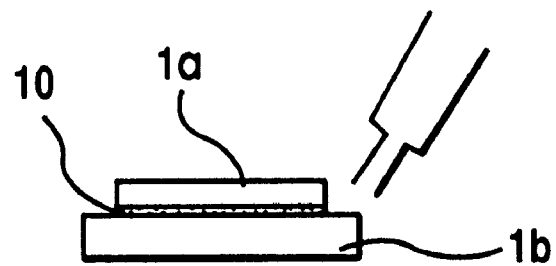
Figure 1D:
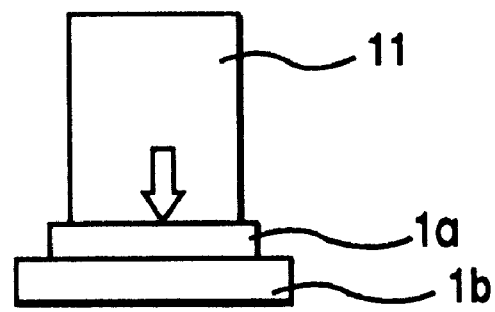
Figure 2A:
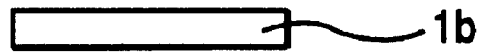
FIG. 2 (A) to FIG. 2 (D) illustrate, with the passage of time, glass substrate bonding steps of the substrate bonding method according to another embodiment of the present invention.
Figure 2B:
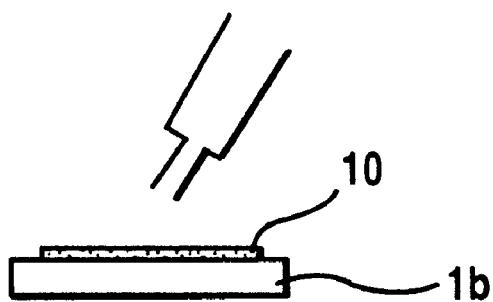
Figure 2C:
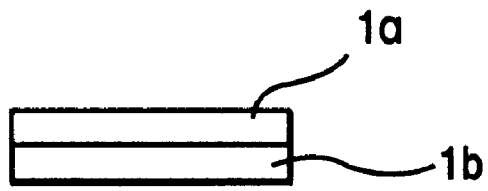
Figure 2D:
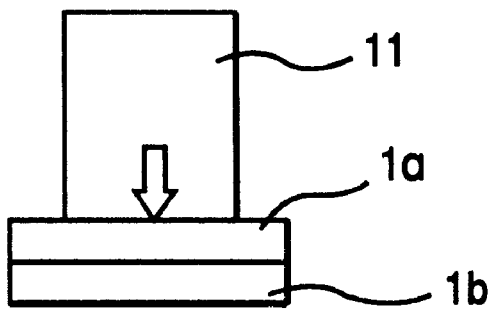

Referring to the drawings, the following description will discuss preferred embodiments of the present invention.

FIG. 1 (A) to FIG. 1 (D) illustrate, with the passage of time, steps of bonding a pair of glass substrates to each other according to the substrate bonding method of a first embodiment of the present invention.

As shown in FIG. 1 (A) and (B), previously cleaned glass substrates 1a, 1b are placed, at a room temperature, one upon another as properly positioned. Preferably, such cleaning is performed with the use of organic matter of acetone or methanol, cleaning with the use of a mixed solution of $H_2SO_4$ and $H_2O_2$, cleaning with the use of a mixed solution of $NH_4OH$, $H_2O_2$ and water, or cleaning with the use of pure water. In particular, cleanings out of the cleanings mentioned above may suitably be combined with each other or one another to enhance the cleaning effect.

Formed in the glass substrate 1b is a groove (not shown) serving as a passage in which a sample is to flow. A metallic layer of aluminium or the like for reflecting light is formed at the groove. To prevent the metallic layer from being damaged by a hydrofluoric acid solution to be dropped at the next step, a protective layer such as a photoresist layer or the like is formed on the top of the metallic layer.

As shown in FIG. 1 (C), a hydrofluoric acid solution or an alkaline solution 10 is dropped to the bonding interface between the glass substrates 1a, 1b. The solution 10 thus dropped spreads uniformly along the bonding interface between the glass substrates 1a, 1b.

Examples of the hydrofluoric acid solution include a mixed solution of hydrofluoric acid and water in which, for example, 1% of hydrofluoric acid is being mixed, a mixed solution of ammonium fluoride and hydrofluoric acid (buffered hydrofluoric acid) and a commercially available undiluted solution of hydrofluoric acid (46%). Examples of the alkaline solution include inorganic alkaline solutions of potassium hydroxide (KOH), sodium hydroxide (NaOH), ammonium hydroxide (NH$_4$OH) and the like, and organic alkaline solutions of tetramethylammonium hydroxide (TMAH) and the like.

As shown in FIG. 1 (D), the glass substrates 1a, 1b are allowed to stand, at a room temperature, for a suitable period of time, e.g., 24 hours, with a load, e.g., 31 gf/cm$^2$, applied to the upper glass substrate 1a using a weight 11. This causes the glass substrates 1a, 1b to be bonded to each other with sufficient strength. When grooves are disposed at the glass substrates, and light reflection metallic layers of aluminium or the like are formed on the respective grooves, the bonded glass substrates may be rinsed with pure water to remove an alkaline solution or a hydrofluoric acid solution which remains on the surfaces of the glass substrates, and the protective resist layers formed on the metallic layers may be removed with acetone.

FIG. 2 (A) to FIG. 2 (D) illustrate, with the passage of time, steps of bonding a pair of glass substrates according to a substrate bonding method of another embodiment of the present invention.

As shown in FIG. 2 (A) and (B), a hydrofluoric acid solution or an alkaline solution 10 is dropped on a glass substrate 1b cleaned as in the embodiment abovementioned. As shown in FIG. 2 (C), a glass substrate 1a is placed on the glass substrate 1b and the glass substrates 1a, 1b are properly positioned with respect to each other. As shown in FIG. 2 (D), the glass substrates are allowed, at a room temperature, to stand for a suitable period of time with a weight 11 placed on the upper glass substrate 1a to apply a load thereto. Thus, the glass substrates 1a, 1b are bonded to each other.

As discussed in the foregoing, the substrate bonding method of the present invention enables glass substrates to be bonded to each other at an ambient temperature. Further, such bonding can be made through a simpler procedure with no use of special heating device and holding means required, as in fusion-bonding.

In particular, even though grooves are disposed at the glass substrates, and light reflection metallic layers of aluminium or the like are formed on the respective grooves, the glass substrates can be bonded to each other without the grooves and metallic layers damaged.

Further, according to the present invention, the glass substrates are bonded to each other by capillary action at the bonding interface thereof. This enables the glass substrates to be uniformly bonded to each other in their entirety.

The foregoing description has been made of the case where glass substrates are bonded to each other. However, the present invention is not limited to such a bonding, but may widely be applied to substrates of which at least bonding surfaces contain silicon dioxide as the primary component. Examples of the substrate materials to be bonded to each other according to the present invention, include quartz to quartz, quartz to borosilicate glass, borosilicate glass to borosilicate glass, quartz to a substrate having a silicon dioxide layer of silicon, a substrate having a silicon dioxide layer of silicon to a substrate having a silicon dioxide layer of silicon, and borosilicate glass to a substrate having a silicon dioxide layer of silicon.

Figure 3A:
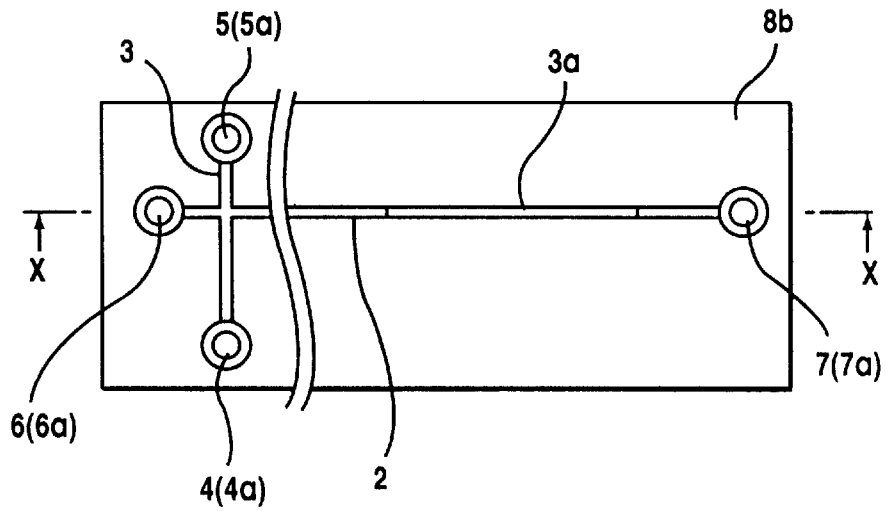
FIG. 3 (A) is a plan view illustrating the arrangement of a detector cell produced according to the substrate bonding method of the present invention.
Figure 3B:
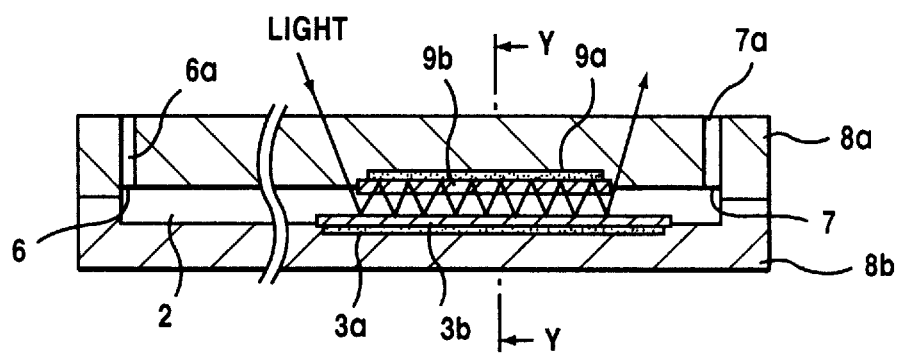
Figure 3C:
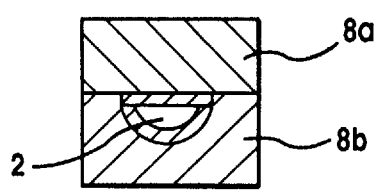
Figure 4A:
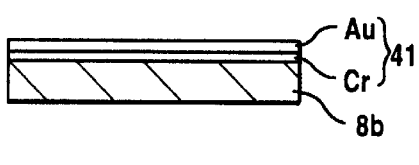
FIG. 4 (A) to FIG. 4 (K) illustrate steps of producing a detector cell according to the substrate bonding method of the present invention.
Figure 4H:
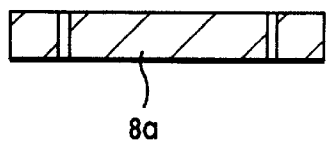
Figure 4B:
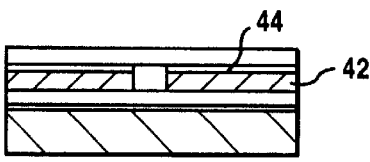
Figure 4I:
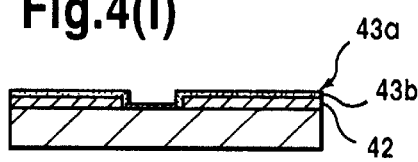
Figure 4C:
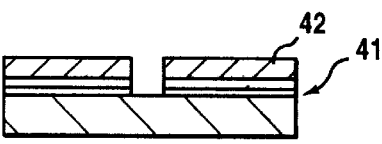
Figure 4D:
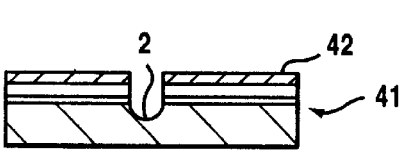
Figure 4J:
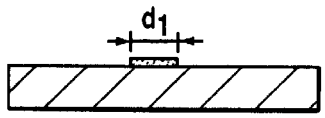
Figure 4E:
Figure 4F:
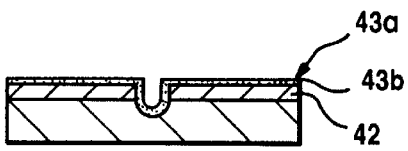
Figure 4G:
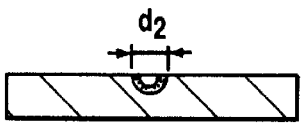
Figure 4K:
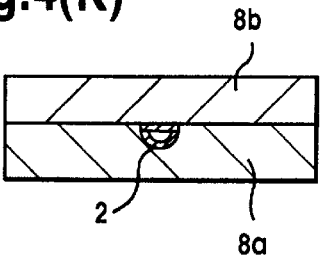

FIG. 3 (A) to FIG. 3 (C) show an embodiment of the present invention in which there is formed a detector cell to be used in a capillary electrophoresis serving as an optical measuring apparatus. FIG. 3 (A) is a plan view of a glass substrate 8a, FIG. 3 (B) is a section view taken along the line X—X in FIG. 3 (A) with glass substrates 8a, 8b put one upon another and FIG. 3 (C) is a section view taken along the line Y—Y in FIG. 3 (B).

In FIG. 3, as each of the glass substrates 8a, 8b, there may be used, for example, a substrate having a length of 10 mm, a width of 20 mm and a thickness of 0.5 mm. Flow channels 2, 3 are formed in each of the glass substrates 8a, 8b by a photofabrication technique. Each of the flow channels 2, 3 has, for example, a width of 70 $\mu$m and a depth of 10 $\mu$m. Reservoirs 4, 5, 6, 7 each having for example a diameter of 1 mm and a depth of 10 $\mu$m, are respectively formed at the ends of the flow channels 2, 3. By an ultrasonic machining for example, through-holes 4a, 5a, 6a, 7a are formed in those positions of the glass substrate 8a corresponding to the reservoirs 4, 5, 6, 7 thereof.

For example, a metallic reflection layer 3a made of aluminium and a protective layer 3b made of quartz are formed at the flow channel 2 of the glass substrate 8b. For example, a metallic reflection layer 9a made of aluminium and a protective layer 9b made of quartz are formed at the glass substrate 8a at positions thereof opposite to those positions of the glass substrate 8b where the metallic reflection layer 3a and the protective layer 3b are formed. Accordingly, ultraviolet rays incident upon the flow channels 2 after transmitted through the glass substrate 8a, are repeatedly reflected by the metallic reflection layers 9a, 3a respectively formed at the glass substrates 8a, 8b, and then left from the glass substrate 8a.

The following description will discuss an electrophoretic measurement made by a capillary electrophoresis having a detector cell having the arrangement above-mentioned.

First, the reservoirs 4, 5, 6, 7 and the flow channels 2, 3 are filled with a sample serving as a substance to be analyzed and a buffer solution which does not absorb light, and needle-like electrodes are inserted in the through-holes 4a, 5a, 6a, 7a of the glass substrate 8a.

An electric field (about 100 V/cm) is applied to the reservoirs 4, 5 such that the sample flows in the flow channels 3, causing the sample to be injected in the flow channels 2. Then, an electric field (about 250 V/cm) is applied to the through-holes 6a, 7a, causing the sample to migrate from the reservoirs 6 to the reservoirs 7 in the flow channels 2. In the course of migration, ultraviolet rays are irradiated from the outside to the metallic reflection layer 3a. The irradiated ultraviolet rays are reflected in a multiple manner by the metallic reflection layers 3a, 9a, and then detected after left to the outside. Those electrically charged particles of the sample separated by electrophoresis, absorb ultraviolet rays in the zone where the metallic reflection layers 3a, 9a are formed in the flow channels 2. Accordingly, as compared with the case of the buffer solution alone, the detected light undergoes a change in intensity such that the separation of electrically charged particles is made sure.

According to the present invention, since the glass substrates 8a, 8b are bonded to each other at a room temperature, the metallic reflection layers 3a, 9a are not damaged in the bonding course. Accordingly, even after the glass substrates 8a, 8b have been bonded, the state of the metallic reflection layers 3a, 9a before bonding, is maintained as it is. Thus, ultraviolet light is hardly absorbed by the metallic reflection layers 3a, 9a, enabling multiple-reflection to be repeated. This assures a highly precise analysis.

Referring to FIG. 4, the following description will discuss how to produce the detector cell above-mentioned.

There is cleaned a glass substrate 8b of quartz which has been annealed for example at 1000° C. for 15 minutes to 4 hours in order to remove processing distortion. As shown in FIG. 4 (A), an etching protective layer 41 of Au (2000 angstroms)/Cr (200 angstroms) for example is continuously formed on the glass substrate 8a using a vacuum evaporator. Then, under the condition of 3000 rpm for 40 seconds, the glass substrate 8b is spin-coated with a photoresist 42 of AZ4620 for example for patterning the etching protective layer 41. The resist thickness is about 7 μm. No particular restrictions are imposed on the material and thickness of the photoresist to be used, but any material and any thickness may be used as far as they can stand a solution used in an etching process to be executed later. Further, no particular restrictions are imposed on the material and thickness of the etching protective layer, but any material and any thickness may be used as far as they can stand a solution used in an etching process to be executed later. Further, means for forming the etching protective layer may be optional as far as the means stands the etching process to be executed later.

As shown in FIG. 4 (B), the photoresist 42 is exposed to light using a photo-mask 44, and then developed. Generally, the photoresist 42 may be exposed to light using an aligner or stepper used in semiconductor production. No particular restrictions are imposed on the developing solution for developing the photoresist 42 as far as it is being used for developing the photoresist 42 to be used.

As shown in FIG. 4 (C), the etching protective layer 41 is patterned using, for example, a mixed solution of iodine, ammonium iodide, water and alcohol for Au, and using, for example, a mixed solution of red prussiate of potash, sodium hydroxide and water for Cr. No particular restrictions are imposed on each etching solution, but any solution may be used as far as Au or Cr is etched without difficulty.

As shown in FIG. 4 (D), using the patterned etching protective layer 41 and the photoresist 42 as masks, the quartz substrate 8b is etched by a commercially available undiluted solution of hydrofluoric acid (46%) for example, thus forming a flow channel 2. No particular restrictions are imposed on the etching solution for quartz, but any solution may be used as far as it etches glass without difficulty.

As shown in FIG. 4 (E) and (F), after the etching protective layer 41 and the photoresist 42 are completely removed, a new photoresist 45 is applied and, as done at the step shown in FIG. 4 (B), the photoresist 45 is exposed to light and then developed to form an opening only at its portion where a reflection layer is to be formed. Then, as a metallic reflection layer 43b, there is formed a layer made of such a material as to sufficiently reflect light in the ultraviolet or visible zone. For example, an Al thin layer (of which thickness is not greater than several 1000 angstroms) is formed. By sputtering for example, there is also formed, as a protective layer 43a, a quartz thin layer (of which thickness is in the range from several 100 angstroms to several 1000 angstroms).

As shown in FIG. 4 (G), the metallic reflection layer 43b and the protective layer 43a are patterned by a lift-off method.

In the foregoing, the description has been made of an example where the flow channel 2 in FIG. 3 is formed. However, the flow channel 3 may also be formed in a similar manner. As shown in FIG. 3, the metallic reflection layer 43b and the protective layer 43a are formed only at a portion of the flow channel 2.

Referring to FIG. 4 (H), the following description will discuss a glass substrate 8a to be bonded to the glass substrate 8b above-mentioned. Through-holes corresponding to the through-holes 6a, 7a and 4a, 5a shown in FIG. 3 are formed in the glass substrate Ba at its predetermined positions using an ultrasonic machining device for example. Then, the glass substrate 8a is cleaned.

As shown in FIG. 4 (I), a metallic reflection layer 43b and a protective layer 43a are formed as done at the steps shown in FIG. 4 (E) and (F). Then, as shown in FIG. 4 (J), these layers 43b, 43a are patterned by a lift-off method as done at the step in FIG. 4 (G).

Each of FIG. 4 (H), (I) and (J) is a section view taken along the flow channel 2. In FIG. 4 (J), each of the metallic reflection layer 43b and the protective layer 43a opposite to the flow channel 2 has a width $d_1$ which is substantially equal to the width $d_2$ of the flow channel 2 of which section is shown in FIG. 4 (G).

As shown in FIG. 4 (K), using the bonding method shown in FIGS. 1 and 2, the both glass substrates are bonded to each other to form a passage and a reflection portion.

Figure 5:
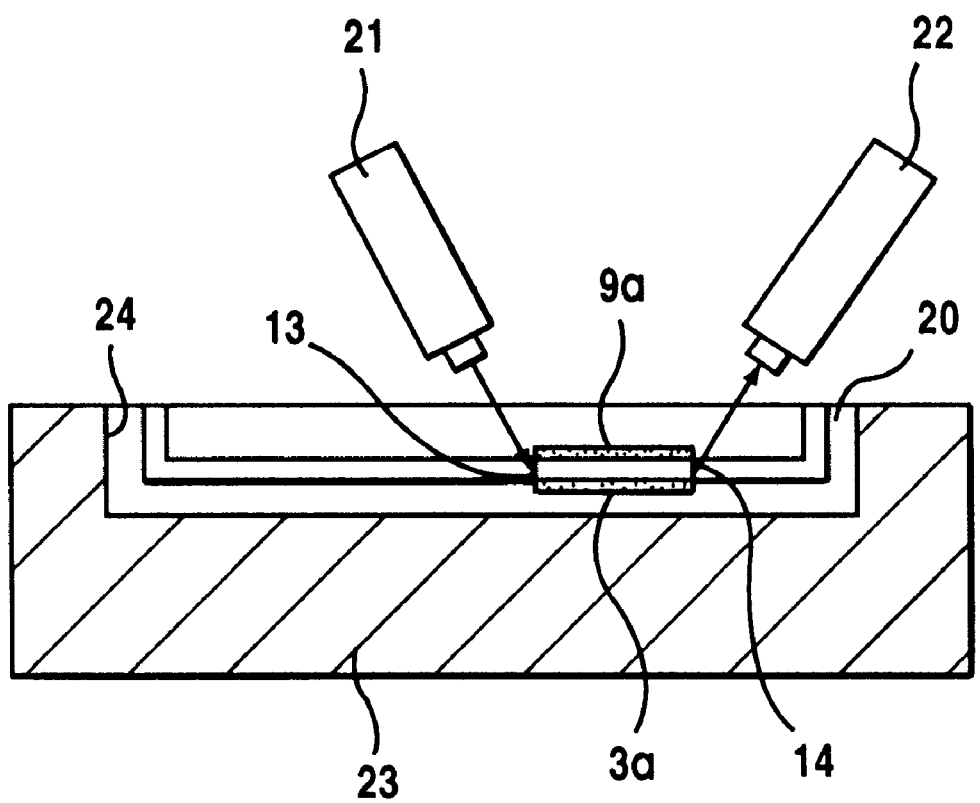
FIG. 5 is a schematic section view illustrating the arrangement of an optical measuring apparatus according to an embodiment of the present invention.

FIG. 5 is a schematic section view illustrating the arrangement of an optical measuring apparatus using the detector cell shown in FIG. 3.

An ultraviolet visible light source 21 is formed by a heavy hydrogen lamp, a tungsten lamp or the like incorporating a spectroscope for emitting light having a predetermined wavelength. A photodetector 22 has a light measuring optical system using a photodiode array detector. These ultraviolet visible light source 21 and photodetector 22 are generally used for measurement of ultraviolet visible light.

A stage 23 has a concave 24 in which a detector cell 20 can be positioned. Accordingly, when the detector cell 20 is inserted into the concave 24, the detector cell 20 can be positioned in the stage 23. Provision is made such that ultraviolet light from the light source 21 can be incident through a light incidence window 13 of the detector cell and that light emitted through a light emission window 14 can be received by the photodetector 22. Thus, by merely setting the detector cell 20 in the concave 24 in the stage 23, optical measurement can be conducted.

We claim:

1. A method of bonding substrates of which at least bonding surfaces contain silicon dioxide as the primary component, comprising the steps of interposing a solution containing hydrofluoric acid for dissolving said substrates between said bonding surfaces, wherein said solution containing hydrofluoric acid is selected from the group consisting of a mixed solution of hydrofluoric acid and water, a buffered hydrofluoric acid and an undiluted solution of hydrofluoric acid.

2. A method of bonding substrates of which at least bonding surfaces contain silicon dioxide as the primary component, comprising the step of interposing a solution for dissolving said substrates between said bonding surfaces, wherein said solution for dissolving said substrates is an alkaline solution.

3. A method of bonding substrates according to claim 2, wherein said alkaline solution is selected from the group consisting of an inorganic alkaline solution and an organic alkaline solution.

4. A method of bonding substrates according to claim 3, wherein said inorganic alkaline solution is selected from the group consisting of a KOH solution, a NaOH solution and a $NH_4OH$ solution.

5. A method of bonding substrates according to claim 3, wherein said organic alkaline solution is tetramethylammonium hydroxide.

6. A method of bonding substrates, of which at least bonding surfaces contain silicon dioxide as the primary component, comprising the step of interposing a solution containing hydrofluoric acid for dissolving said substrates between said bonding surfaces, the solution containing hydrofluoric acid being selected from the group consisting of a mixed solution of hydrofluoric acid and water, a buffered hydrofluoric acid and an undiluted solution of hydrofluoric acid, wherein a pair of said substrates to be bonded to each other using said solution containing hydrofluoric acid is selected from the group consisting of a pair of quartz and quartz, a pair of quartz and borosilicate glass, a pair of borosilicate glass and borosilicate glass, a pair of quartz and a substrate having an oxide layer of silicon, a pair of substrates each having an oxide layer of silicon and a pair of borosilicate glass and a substrate having an oxide layer of silicon.

7. A method of bonding substrates according to any one of claims 2, 3, 4 and 5, wherein a pair of said substrates to be bonded to each other using said alkaline solution, is selected from the group consisting of a pair of quartz and quartz, a pair of quarts and borosilicate glass, a pair of borosilicate glass and borosilicate glass, a pair of quartz and a substrate having an oxide layer of silicon, a pair of substrates each having an oxide layer of silicon and a pair of borosilicate glass and a substrate having an oxide layer of silicon.

8. A method of bonding substrates according to any of claims 1 to 5, wherein said substrates to be bonded consist of at least one pair of glass substrates which have been cleaned, and a groove is formed in the bonding surface of one of said glass substrates.

9. A method of bonding substrates according to claim 8, wherein said cleaning is selected from the group consisting of cleaning with the use of organic matter acetone or methanol, cleaning with the use of a mixed solution of $H_2SO_4$ and $H_2O_2$, cleaning with the use of a mixed solution of $NH_4OH$, $H_2O_2$ and water, cleaning with the use of pure water, and a combination of cleanings out of the above-mentioned cleanings.

10. A method of bonding substrates according to claim 8 comprising the additional steps of:

forming a metallic layer on a surface of said groove; and
forming a protective resist layer on said metallic layer.

* * * * *